US005266559A

United States Patent [19]

Fankhauser et al.

[11] Patent Number: 5,266,559

[45] Date of Patent: Nov. 30, 1993

[54] USE OF UNSATURATED MACROCYCLIC LACTONES AS PERFUMING INGREDIENTS

[75] Inventors: Peter Fankhauser, Meyrin, Switzerland; Piero Fantini, La Jolla, Calif.

[73] Assignee: Firmenich S.A., Geneva, Switzerland

[21] Appl. No.: 972,038

[22] Filed: Nov. 5, 1992

Related U.S. Application Data

[63] Continuation of Ser. No. 602,437, Oct. 23, 1990.

[30] Foreign Application Priority Data

Oct. 27, 1989 [CH] Switzerland ........................ 3894/89

[51] Int. Cl.[5] ............................................... A61K 7/46
[52] U.S. Cl. ....................................................... 512/11
[58] Field of Search ........................................... 512/11

[56] References Cited

U.S. PATENT DOCUMENTS

| | | | |
|---|---|---|---|
| 3,890,353 | 6/1975 | Becker | 260/343 |
| 4,568,470 | 2/1986 | Van Loveren et al. | 252/8.6 |

FOREIGN PATENT DOCUMENTS

| | | | |
|---|---|---|---|
| 55-083778 | 6/1980 | Japan | 512/266 |
| 7407463 | 8/1974 | Netherlands | 512/266 |
| 922409 | 4/1963 | United Kingdom | 549/266 |

OTHER PUBLICATIONS

S. L. Schreiber et al., J. Amer. Chem. Soc. 102, 6163 (1980).
S. L. Schreiber et al., J. Amer. Chem. Soc. 107, 2980 (1985).

*Primary Examiner*—James H. Reamer
*Attorney, Agent, or Firm*—Pennie & Edmonds

[57] ABSTRACT

Perfuming composition or perfumed article containing as a perfuming ingredient at least one pentadecenolide of formula (I)

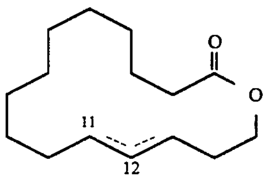

having a double bond of trans configuration in one of the positions 11 or 12 such as indicated by the dotted lines. Compounds (I) develop musky, animal odor notes, reminiscent of natural musk.

13 Claims, No Drawings

USE OF UNSATURATED MACROCYCLIC LACTONES AS PERFUMING INGREDIENTS

This is a continuation of application Ser. No. 07/602,437, filed Oct. 23, 1990.

BRIEF SUMMARY OF THE INVENTION

The present invention relates to the perfume industry. More particularly, it provides a method to confer, improve, enhance or modify the odor properties of a perfuming composition or a perfumed article, which method comprises adding to said composition or article a fragrance effective amount of a pentadecenolide of formula (I)

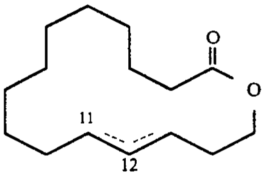

having a double bond of trans configuration in one of the positions 11 or 12 such as indicated by the dotted lines.

The invention further provides a perfuming composition or a perfumed article containing as a perfuming ingredient a compound or a mixture of compounds of formula (I).

BACKGROUND OF THE INVENTION

The compounds of formula (I) are unsaturated macrocyclic lactones of known chemical structure. They have in fact been cited as by-products or intermediate compounds in a process for the preparation of fragrant saturated macrolides such as pentadecanolide, known commercially under the tradename of EXALTOLIDE® (origin: Firmenich SA, Geneva, Switzerland), and analogues thereof [see, for example, U.S. Pat. No. 3,890,353 or J. Becker and G. Ohloff, Helv. Chim. Acta, 2889, (1971)]. According to this prior art process, an appropriate peroxide was cleaved by means of thermal or radiation energy, or yet of chemical agents, to provide a mixture containing the desired saturated lactones, as well as their unsaturated counterparts. The saturated lactones were then either separated from the mixture via the usual techniques, or obtained by hydrogenation of said mixture or of the unsaturated lactones there-contained. As it was formulated, the prior art process provided a solution to the problem of preparing EXALTOLIDE® and analogues thereof, while the corresponding unsaturated derivatives obtained simultaneously were actually undesirable products of the same process. Since the individual olfactive properties of said unsaturated lactones as such were not recognized at the time, the process comprised a systematic hydrogenation step adapted to convert said unsaturated derivatives into the desired saturated lactones. Furthermore, this hydrogenation step was in fact claimed as an essential characteristic of the prior art process.

THE INVENTION

It has now been discovered that the above-mentioned unsaturated lactones, and more particularly those having a trans configuration, i.e. trans-pentadec-12-en-15-olide and trans-pentadec-11-en-15-olide, possess very useful odor properties and that, as a result, they can be advantageously used for the preparation of perfuming compositions and perfumed articles.

Accordingly, the present invention provides a method to confer, improve, enhance or modify the odor properties of a perfuming composition or a perfumed article, which method comprises adding to said composition or article a fragrance effective amount of at least one pentadecenolide of formula (I)

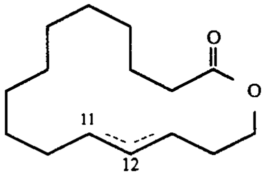

having a double bond of trans configuration in one of the positions 11 or 12 such as indicated by the dotted lines.

It has now been established that these unsaturated lactones and their mixtures develop odor notes of musky and animal character, unusually powerful and effective for this type of fragrances. When compared to each other, these two lactones are found to possess similar odor qualities, the odor of trans-pentadec-11-en-15-olide being somewhat less powerful than that of trans-pentadec-12-en-15-olide, the latter also having a more pronounced musk-ambrette and fruity-pear odor character and being preferred according to the invention.

When compared to their saturated analogue, i.e. pentadecanolide or EXALTOLIDE®, the pentadecenolides mentioned above possess musky odor notes of a clearly more animal character, with a connotation reminiscent of natural musk. Furthermore, they have the advantage of possessing odors which are much more powerful and tenacious, and have more volume, than the odor characteristic of pentadecanolide. In particular, the substantivity of their note turns out to be not only clearly greater than that of EXALTOLIDE®'s note, but also than that of the musky note characteristic of a well-known and appreciated aromatic compound, i.e. GALAXOLIDE® 50 IPM (1,3,4,6,7,8-hexahydro-4,6,6,7,8,8-hexamethylcyclopenta-γ-2-benzopyran; origin: IFF Inc.), as becomes apparent from the examples presented further on.

When comparing pentadecenolides (I) and their mixtures with another macrolide, i.e. pentadec-10-en-15-olide, known from U.S. Pat. Nos. 4,490,404, 4,541,950, 4,559,168 and 4,568,470, it was also observed that the above-mentioned chemical compositions of the present invention possessed clearly superior odor properties to those of the cited prior art compound. The latter possessed in fact a much weaker and less tenacious musky note, also more aldehydic and slightly fat. The odor of pentadec-10-en-15-olide was reminiscent of that of cyclopentadecanone, commercialized under the tradename of EXALTONE® (origin: Firmenich SA, Geneva), and was totally devoid of the musk-ambrette, fruity-pear character that renders the compounds of the present invention particularly interesting.

On the other hand, it has also been observed that the compounds of formula (I) have distinct odors from those of their isomers represented by the formula

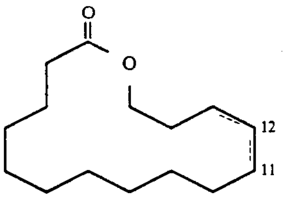

(II)

having a double bond of cis configuration in one of the positions 11 or 12 such as indicated by the dotted lines. Compounds (II) have in fact musky type odor notes which are less animal and elegant, as well as weaker, than those of the corresponding trans-pentadecenolides (I).

The unsaturated macrocyclic lactones mentioned above can be used in a variety of perfumery applications. They are equally useful for the preparation of perfumes and Colognes, as for perfuming functional products such as soaps, bath or shower gels, shampoos, air or body deodorants, cosmetic preparations or household products. As a result of their note's substantivity, they are particularly advantageous for perfuming detergents or fabric softeners.

In these applications, lactones (I) can be used on their own or in admixture with one or several perfuming coingredients, solvents or the usual carriers. In particular, these pentadecenolides form harmonious mixtures with each other, or yet with their saturated counterpart pentadecanolide. When mixed together, trans-pentadec-11-en-15-olide and trans-pentadec-12-en-15-olide may be present in the mixtures in a wide variety of relative proportions. Mixtures which contain equivalent amounts of trans-pentadec-11-en-15-olide and trans-pentadec-12-en-15-olide, or a surplus of the latter, have been found to be olfactively excellent, with an odor quality which is comparable to that of their individual components. Nevertheless, we observed that admixing these two pentadecenolides in relative proportions other than the above-mentioned made it possible to obtain excellent perfuming mixtures whose qualities were still judged superior to those of EXALTOLIDE® and still advantageous for the applications according to the present invention.

On the other hand, even if the cis isomers of formula (II) possess less animal and less powerful musky odors than those of pentadecenolides (I), their presence in isomeric mixtures is in no way detrimental to the global olfactive effect as long as the said mixtures contain a predominant amount of trans configuration pentadecenolides (I), i.e., their content in the latter is at least 60% by weight, relative to the total weight of the mixture. Among such mixtures of unsaturated isomers those which have a global content in pentadecenolides (I) of the order of 70% by weight or more are preferred according to the invention. Such mixtures of the four isomers develop a very powerful musky note with an ambrette connotation.

The invention thus concerns equally the use as perfuming ingredients of such mixtures of isomers of cis and trans configuration, as well as that of the mixtures described hereinafter which also contain pentadecanolide. These are, in fact, fragrance ingredients the qualities of which are quite convenient for the applications of the invention and which present the advantage of being less costly than the other chemical compositions according to the invention, since they can be directly obtained from the synthesis described further on, without requiring separation of the individual components.

Whenever trans-pentadec-12-en-15-olide or trans-pentadec-11-en-15-olide, or a mixture thereof or having a preponderant amount of these lactones, was added to EXALTOLIDE®, new perfuming ingredients were obtained whose musky note was more powerful and tenacious, while the animal connotation was also enhanced. Depending on the desired perfuming effect, it has been found that the mentioned saturated and unsaturated lactones could be mixed in a wide range of proportions without prejudice for the olfactive harmony of the mixture. Furthermore, the cited enriching effect, from the olfactive point of view, of admixing the pentadecenolides could be observed even for weak concentrations of the latter, say, of the order of 5% by weight or even less, relative to the weight of EXALTOLIDE®.

In order to achieve the desired perfuming effects, trans-pentadec-12-en-15-olide, trans-pentadec-11-en-15-olide or their mixtures can be used according to the invention in a wide variety of concentrations for preparing perfuming compositions or perfuming articles. The man in the art is well aware that such concentration values are a function of the nature of the product to be perfumed, as well as of that of the other coingredients in a given composition. One can cite, in this context, lactone concentrations of the order of 1 to 10%, or even 20% by weight, relative to the weight of the composition into which said lactones are incorporated. Much lower values can be used whenever these lactones are used for perfuming consumer articles such as soaps and shower or bath gels, shampoos, cosmetic preparations or detergents and fabric softeners.

The unsaturated macrocyclic lactones of formula (I) or (II) can be prepared from 2-(3-hydroxypropyl)-1-cyclododecanone (prepared as described in U.S. Pat. No. 3,890,353) following a method analogous to that described by S. L. Schreiber et al. in J. Amer. Chem. Soc. 102, 6163 (1980) and 107, 2980 (1985) for the preparation of macrolides. The specific preparation conditions were the following.

A 4-neck flask equipped with mechanical stirring, an inlet funnel, a thermometer, a condenser and kept under nitrogen, was charged with 30 g (125 mmol) of 2-(3-hydroxypropyl)-1-cyclododecanone and 137.5 g (2.29 mol) of glacial acetic acid. The mixture was stirred at room temperature until it became homogeneous. A cooled mixture of water (12.5 g) and a 50% aqueous solution of sulphuric acid (12.5 g) was then added. The reaction mixture was cooled to 0° C. and then 10 ml of 70% oxygenated water were added thereto dropwise over 15 min; the temperature rose to 7° C. Once the introduction was completed, stirring was continued for 15 min at 0° C. The formed precipitate was filtered, washed with water and then with diluted aqueous $NaHCO_3$. 62.0 G of wet product were thus obtained which, after drying, provided 25.6 g (yield 80%) of 14a-hydroperoxy-cyclododeca[b]-pyran which was used in the following step. M. p.: 104°-106° C.

Analytical data

IR(KBr): 3320, 2920, 2850, 1465, 1445, 1430, 1415, 1370, 1350, 1310, 1280, 1250, 1220, 1205, 1190, 1180, 1160, 1150, 1120, 1090, 1080, 1055, 1015, 980, 950, 900, 870, 840, 795, 725, 640, 595 $cm^{-1}$

NMR($^1H$,360 MHz,$CDCl_3$): 7.39, 7.40(2 s,1H); 3.84–3.70(m,2H); 2.06–1.94 (m,1H); 1.88–1.00(m,24H) δ ppm NMR($^{13}C$,360 MHz,$CDCl_3$): 107.96(s); 61.55(t); 36.07(d); 28.88(t); 26.66(t); 26.29(t); 26.22(t); 25.72(t); 25.00(t); 24.10(t); 22.55(t); 22.39(t); 21.64(t); 19.62(t) δ ppm MS: 238($M^+$—$H_2O$,1), 223(23), 210(1), 197(3), 178(1), 161(2), 151(3), 137(4), 123(9), 109(15), 95(32), 81(41), 71(86), 55(100), 41(64)

In a 3-neck flask equipped with magnetic stirring, a thermometer, a condenser and maintained under nitrogen, a saturated solution of cupric acetate [$Cu(CH_3COO)_2$, 8.5 g] was prepared in methanol (200 ml). The solution was filtered to separate the non-dissolved salt. 12.8 g (50 mmol) of 14a-hydroxyperoxy-cyclododeca[b]-pyran were added by portions to the blue solution and, after stirring for 30 min, 1.5 g of $FeSO_4$, followed, 2 h later, by yet another 1.5 g of $FeSO_4$. The reaction mixture was left under stirring overnight at room temperature. It was then poured on sat. aqueous NaCl, extracted with isopropyl ether and washed with sat. aqueous NaCl and sat. aqueous $NaHCO_3$. The organic phase was dried over $Na_2SO_4$, filtered and concentrated. 11.4 g of raw product were thus obtained which were then distilled on a Vigreux column to yield 8.7 g of pure product. The analysis of this product showed that it consisted of a mixture containing around 43% of trans-pentadec-11-en-15-olide, 26% of trans-pentadec-12-en-15-olide, 18% of cis-pentadec-11-en-15-olide, 5% of cis-pentadec-12-en-15-olide and 8% of pentadecanolide.

B.p.: 88°–93° C./40 Pa.

This mixture was separated by chromatography on a capillary column DBWax having 30 m length and 0.53 mm diameter, using He (50 KgPa) as the carrying gas, to provide the above-mentioned trans-pentadecenolides in a pure state and a mixture of the two cis-pentadecenolides cited above.

The analytical data of these compounds were as follows:

trans-pentadec-11-en-15-olide

Retention time: 25.35 min

NMR($^1H$,360 MHz,$CDCl_3$): 1.18–1.42(m,10H); 1.72(m,4H); 1.75(m,2H); 2.04(m,2H); 2.18(m,2H); 2.34(m,2H); 4.10(t,J≈6 Hz,2H); 5.36(dt, J≈16,6 Hz,1H); 5.41(dt,J≈16,6 Hz,1H) δ ppm MS: 238($M^+$,6), 178(2), 150(4), 136(4), 123(7), 109(12), 95(36), 81(80), 68(100), 55(49), 41(54)

trans-pentadec-12-en-15-olide

Retention time: 25.59 min

NMR($^1H$,360 MHz,$CDCl_3$): 1.18–1.70(m,16H); 2.06(m,2H); 2.30(t,J≈7 Hz,2H); 2.32(m,2H); 4.11(t,J≈5 Hz,2H); 5.44(m,2H) δ ppm MS: 238($M^+$,5), 178(1), 150(3), 136(4), 123(12), 109(16), 95(36), 82(63), 68(100), 55(64), 41(60)

cis-pentadec-11-en-15-olide (A) and
cis-pentadec-12-en-15-olide (B)

Retention time: 26.11 min

NMR($^1H$,360 MHz,$CDCl_3$): 1.18–1.72(m); 1.67(m,2H,A); 2.04(m,2H of A and 2H of B); 2.19(m,2H,A); 2.30(t,J≈7 Hz,2H,B); 2.35(t,J≈6 Hz,2H,A); 2.41(m,2H,B); 4.12(t,J≈6 Hz,2H,B); 4.14(t,J≈6 Hz,2H,A); ≈5.3–5.6(m,2H,B); 5,34(m,1H,A); 5,41(m,1H,A) δ ppm MS: 238($M^+$,5), 178(1), 150(4), 136(4), 123(7), 109(14), 95(35), 81(66), 68(100), 55(54), 41(57)

The invention will now be described in further detail by way of the following non-restrictive examples, wherein trans-pentadec-12-en-15-olide, trans-pentadec-11-en-15-olide, as well as their mixtures according to the invention, are designated by the generic term of (E,Z)-pentadec-11(12)-en-15-olide. We established, in fact, that, despite the olfactive variations mentioned before observed between the various isomers, the conclusions reached through the comparative essays described in these examples were equally valid for anyone of the above-mentioned chemical compositions.

EXAMPLE 1

Test of Substantivity on Fabric

To a non-perfumed standard fabric softener, there was added, respectively (E,Z)-pentadec-11(12)-en-15-olide, EXALTOLIDE ® (origin: Firmenich SA, Switzerland) and GALAXOLIDE ® 50 IPM (origin: IFF Inc.), in the quantities indicated in the following Table (parts by weight), in order to prepare three samples of a perfumed fabric softener.

TABLE

| Ingredients | Sample 1 | Sample 2 | Sample 3 |
|---|---|---|---|
| Non-perfumed standard softener | 99.9 | 99.9 | 99.8 |
| (E,Z)-Pentadec-11(12)-en-15-olide | 0.1 | — | — |
| EXALTOLIDE ® | — | 0.1 | — |
| GALAXOLIDE ® 50 IPM | — | — | 0.2 |

Three standard mixed fabric batches, containing cotton, acrylic and nylon textiles, were separately treated in three washing machines with, respectively, samples 1, 2 and 3 prepared as mentioned above. The three fabric batches were then submitted to a blind evaluation test carried out by seven expert perfumers. They were evaluated both wet and after drying of the textiles.

The results of the evaluation test showed that, according to six of the seven perfumers, the textile batch treated with sample 1, which contained (E,Z)-pentadec-11(12)-en-15-olide, developed a much stronger odor immediately after being taken out of the washing machine, an odor which also remained much longer on the dried textiles, than that of the fabric batch treated with sample 3, which contained GALAXOLIDE ® 50 IPM. Only one perfumer preferred this latter batch.

On the other hand, the evaluation of the fabric batch treated with sample 1 with respect to the batch treated with sample 2 containing EXALTOLIDE ® also confirmed the superiority of the odor note of (E,Z)-pentadec-11(12)-en-15-olide, from a strength and substantivity point of view, over that of EXALTOLIDE ®'s, since the perfumers were unanimous in their preference for the firstly mentioned batch of fabrics.

EXAMPLE 2

Preparation of a Masculine Cologne

A musky type base perfuming composition for a masculine Cologne was prepared by admixture of the following ingredients:

| Ingredients | Parts by weight |
|---|---|
| Benzyl acetate | 20 |
| 50%* Cinnamic alcohol | 50 |
| 10%* n-Octanal | 5 |

-continued

| Ingredients | Parts by weight |
|---|---|
| 10%* n-Decanal | 25 |
| 10%* n-Dodecanal | 30 |
| Hexylcinnamic aldehyde | 40 |
| 10%* Hydroxycitronellal methylantranilate | 20 |
| Bergamot essential oil | 80 |
| Lemon essential oil | 30 |
| Coumarin | 10 |
| 10%* Ethylvanilline | 25 |
| 10%* Galbanum essential oil | 25 |
| LILIAL ®[1)] | 50 |
| IRALIA ®[2)] | 20 |
| Labdanum essential oil | 10 |
| Lavender absolute | 50 |
| Mint essential oil | 5 |
| Methyl everninate | 20 |
| HEDIONE ®[3)] | 100 |
| Petitgrain essential oil | 5 |
| Terpineol | 15 |
| Iso E Super[4)] | 55 |
| α-Ionone | 10 |
| 10%* AMBROX ® DL[5)] | 20 |
| Ylang essential oil | 10 |
| Clary sage essential oil | 25 |
| Jasmine absolute | 10 |
| Lavender essential oil | 35 |
| Total | 800 |

*in dipropylene glycol
1) 3-(4-tert-butyl-1-phenyl)-2-methylpropanal; origin: L. Givaudan SA, Vernier, Switzerland
2) methylionone; origin: Firmenich SA, Geneva, Switzerland
3) methyl dihydrojasmonate; origin: Firmenich SA, Geneva, Switzerland
4) 2-acetyl-1,2,3,4,5,6,7,8-octahydro-2,3,8,8-tetramethylnaphthalene; origin: IFF Inc.
5) tetramethyl perhydronaphthofuran; origin: Firmenich SA, Geneva, Switzerland A new composition A was prepared by adding 400 parts by weight of (E,Z)-pentadec-11(12)-en-15-olide to this base composition, while a composition B was prepared by admixture to the same base composition of 400 parts by weight of EXALTOLIDE ®.

A panel of expert perfumers evaluated and compared compositions A and B. Their unanimous judgement was that composition A had a much more musky, animal and powerful odor note than composition B.

What we claim is:

1. A method to impart a musk-ambrette, fruity pear fragrance character to a perfuming composition or a perfumed article, which method comprises adding to said composition or article a fragrance effective amount of a perfuming agent consisting essentially of a trans-pentadecenolide of formula (Ia)

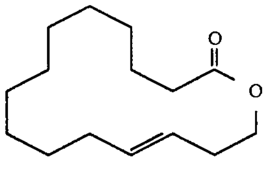

to impart said musk-ambrette, fruity pear fragrance character to said composition or perfumed article.

2. The method of claim 1 wherein the perfuming agent consists of the trans-pentadecenolide of formula Ia.

3. A method to impart a musk-ambrette, fruity pear fragrance character to a perfuming composition or a perfumed article, which method comprises adding to said composition or article a fragrance effective amount of a perfuming agent consisting essentially of a trans-pentadecenolide of formula (Ib)

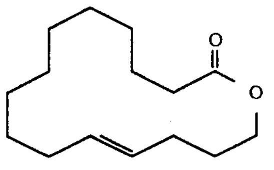

to impart said musk-ambrette, fruity pear fragrance character to said composition or perfumed article.

4. The method of claim 3 wherein the perfuming agent consists of the trans-pentadecenolide of formula Ib.

5. A method to impart a musk-ambrette, fruity pear fragrance character to a perfuming composition or a perfumed article, which method comprises adding to said composition or article a fragrance effective amount of a perfuming agent mixture containing a pentadecenolide of formula (Ia)

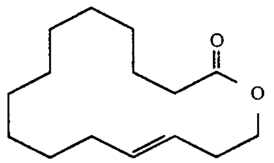

together with an equivalent or lesser amount of a pentadecenolide of formula (Ib)

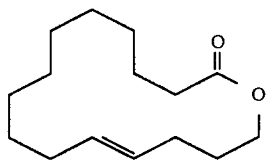

to impart said musk-ambrette, fruity pear fragrance character to said composition or perfumed article.

6. A method to impart a musk-ambrette, fruity pear fragrance character to a perfuming composition or a perfumed article, which method comprises adding to said composition or article a fragrance effective amount of a mixture containing a predominant amount of pentadecenolides of formula

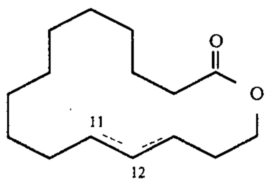

having a double bond of trans configuration in one of the positions 11 or 12 such as indicated by the dotted lines, together with lesser amounts of a pentadecenolide of formula

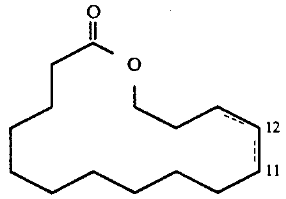
(II)

having a double bond of cis configuration in one of the positions indicated by the dotted lines to impart said musk-ambrette, fruity pear fragrance character to said composition or perfumed article.

7. The method of claim 6 wherein the pentadecenolides of formula I are a mixture of trans-pentadec-12-en-15 olide and trans-pentadec-11-en-15-olide.

8. The method of claim 7 wherein the trans-pentadec-11-en-15-olide is present in an amount which is equal to or greater than that of the trans-pentadec-12-en-15-olide.

9. The method of claim 6 wherein the formula (I) pentadecenolides are present in an amount of at least about 70% by weight of said mixture.

10. The method of claim 6 wherein said mixture contains about 43% by weight of trans-pentadec-11-en-15-olide, 26% by weight of trans-pentadec-12-en-15-olide, 18% by weight of cis-pentadec-11-en-15-olide and 5% by weight of cis-pentadec-12-en-15-olide.

11. A perfuming composition containing as a perfuming ingredient a pentadecenolide or a mixture of pentadecenolides as defined in any one of claims 1 to 7.

12. A perfumed article containing as a perfuming ingredient a pentadecenolide or a mixture of pentadecenolides as defined in any one of claims 1 to 7.

13. The perfume article of claim 12 in the form of a perfumed or a Cologne, a soap, a shower or bath gel, a shampoo, a cosmetic preparation, an air or body deodorant, a detergent or a fabric softener, or a household product.

* * * * *